United States Patent [19]
Yeager

[11] Patent Number: 5,390,791
[45] Date of Patent: Feb. 21, 1995

[54] TEMPERATURE CONTROLLED MEDECINE CARRIER

[75] Inventor: Steve Yeager, Redondo Beach, Calif.

[73] Assignee: Medicool, Inc., Torrance, Calif.

[21] Appl. No.: 139,298

[22] Filed: Oct. 18, 1993

[51] Int. Cl.⁶ .................. A61B 17/06; A61B 19/02; B65D 81/02

[52] U.S. Cl. .................. 206/438; 206/523; 206/570; 206/828; 62/457.1; 62/457.9

[58] Field of Search .............. 62/457.1, 457.2, 457.5, 62/457.9; 206/570, 438, 828

[56] References Cited

U.S. PATENT DOCUMENTS

| | | | |
|---|---|---|---|
| 4,250,998 | 2/1981 | Taylor | 206/828 X |
| 4,322,954 | 4/1982 | Sheehan et al. | 206/828 X |
| 4,343,158 | 8/1982 | Campbell | 206/828 X |
| 4,429,793 | 2/1984 | Ehmann | 206/828 X |
| 4,738,364 | 4/1988 | Yeager | 206/828 X |
| 4,955,480 | 9/1990 | Sexton | 62/457.9 |
| 5,216,900 | 6/1993 | Jones | 62/457.2 |

Primary Examiner—William I. Price
Attorney, Agent, or Firm—Hecker & Harriman

[57] ABSTRACT

A portable medicine carrier and protector for storing and transporting medicine stored in vials. The vials may be of different sizes. The medicine carrier and protector includes a hollow, thin walled medicine carrier. The carrier is substantially filled with a paraffinic hydrocarbon (C14–C18) such as Hexadecane, an alpha olefin (C14–C20), or a material such as Dimethyl Sulfoxide. A cavity is disposed in a top surface of the carrier. The cavity being formed from a plurality of different semi-circular compartments. Each of the compartments has a different cross-sectional radius. This allows the carrier to accept medicine vials of differing sizes. A plurality of solid ribbed members are disposed transversely in the cavity, so as to prevent direct contact between the carrier and the medicine vials.

10 Claims, 19 Drawing Sheets

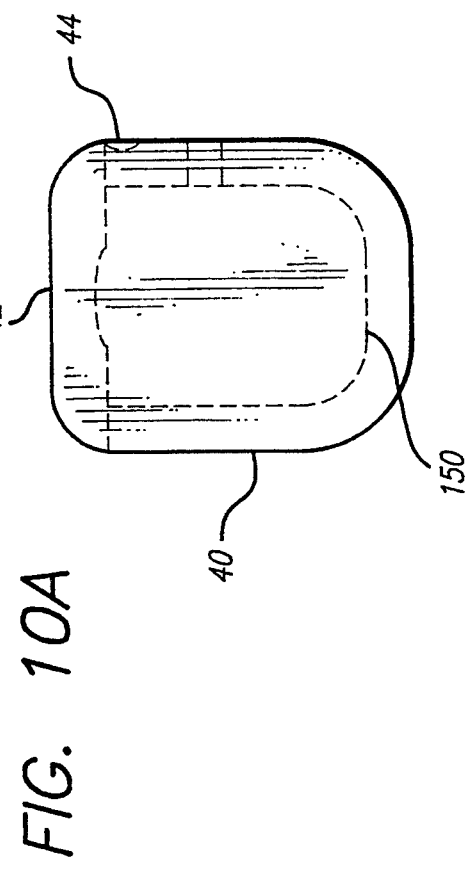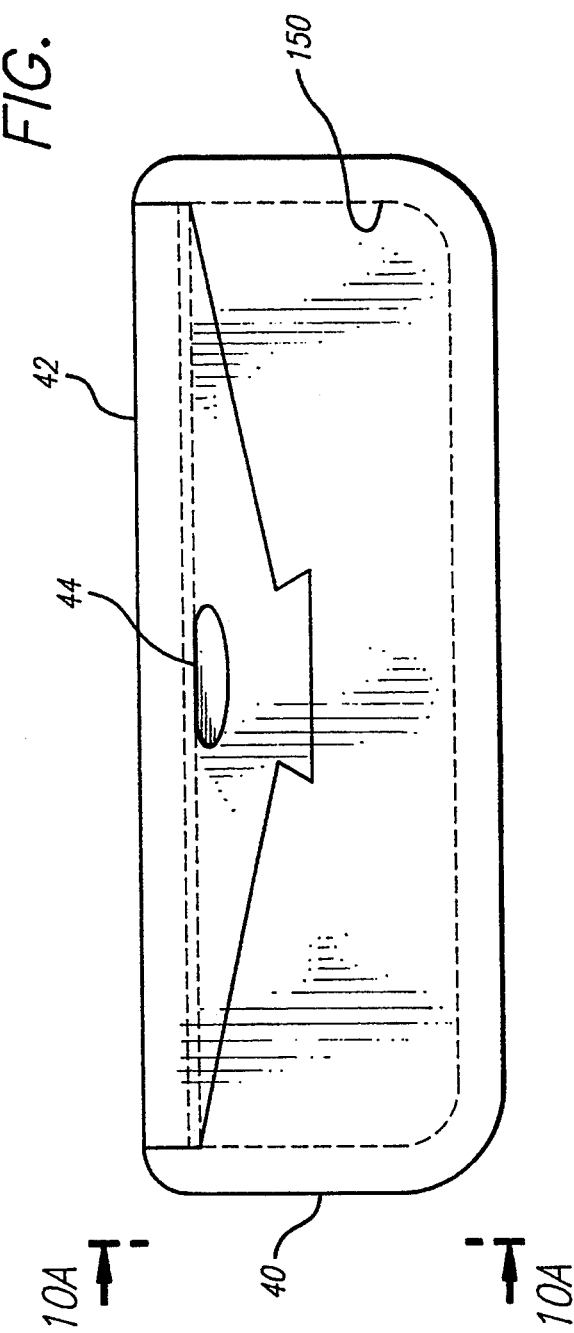

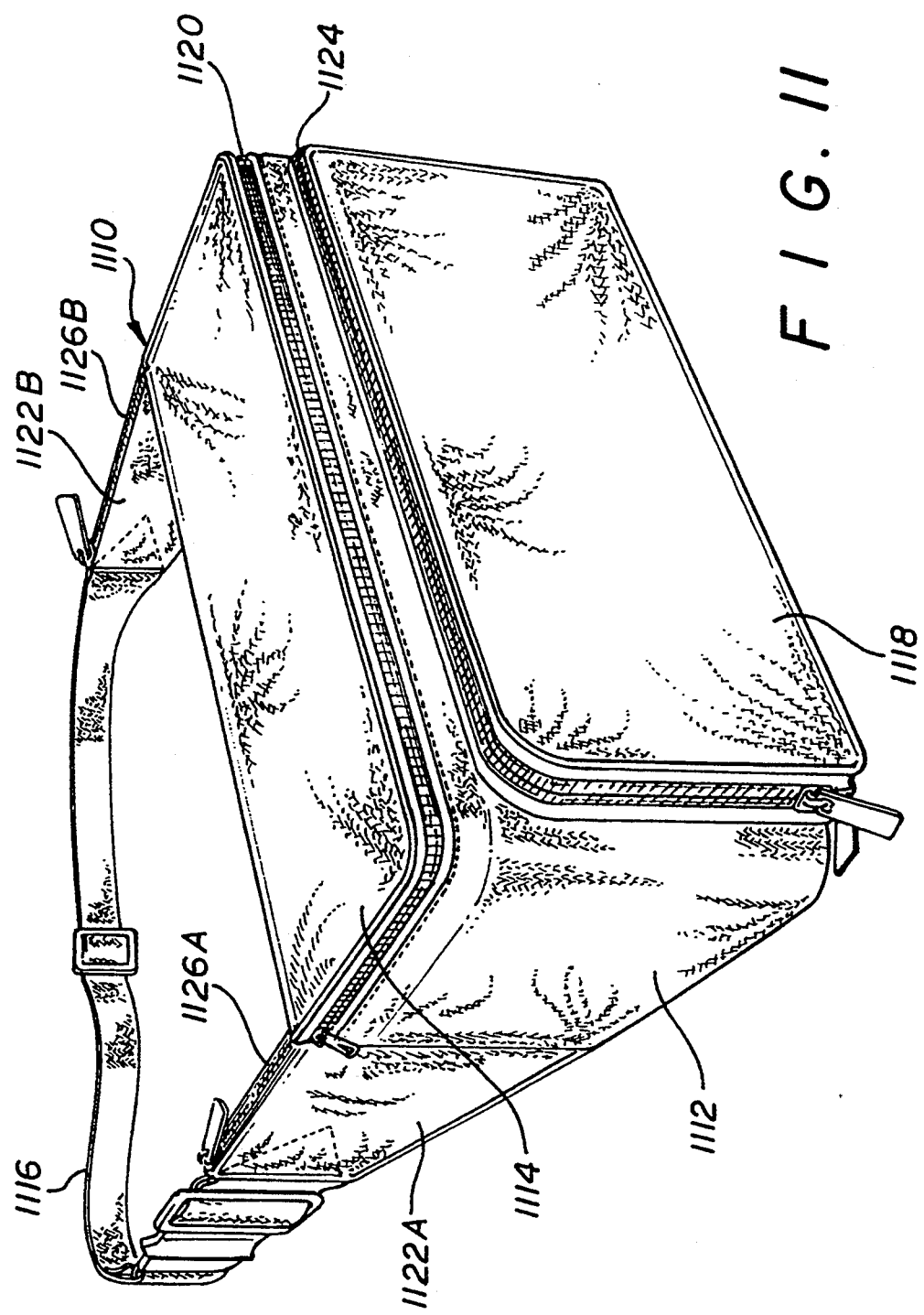

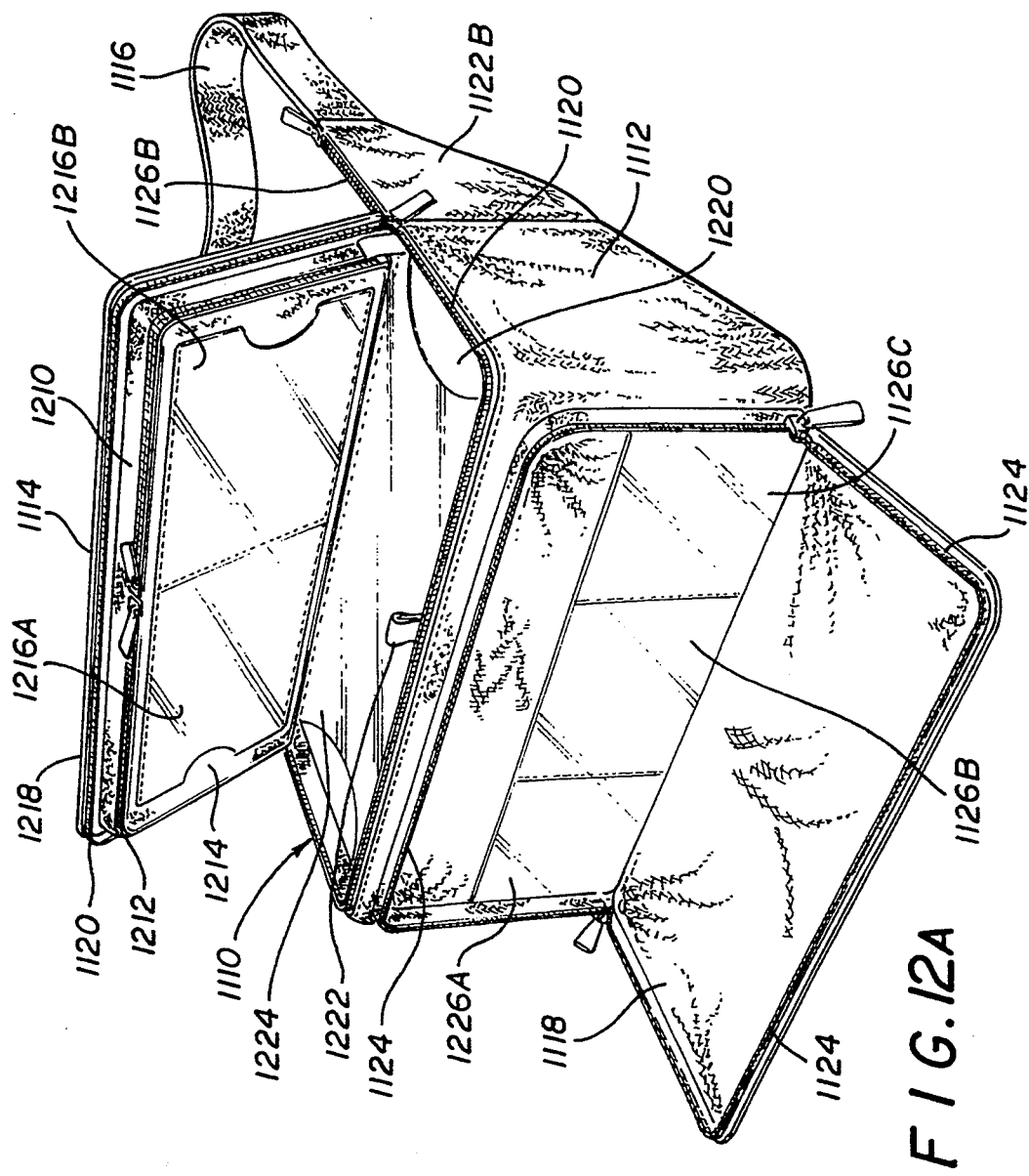

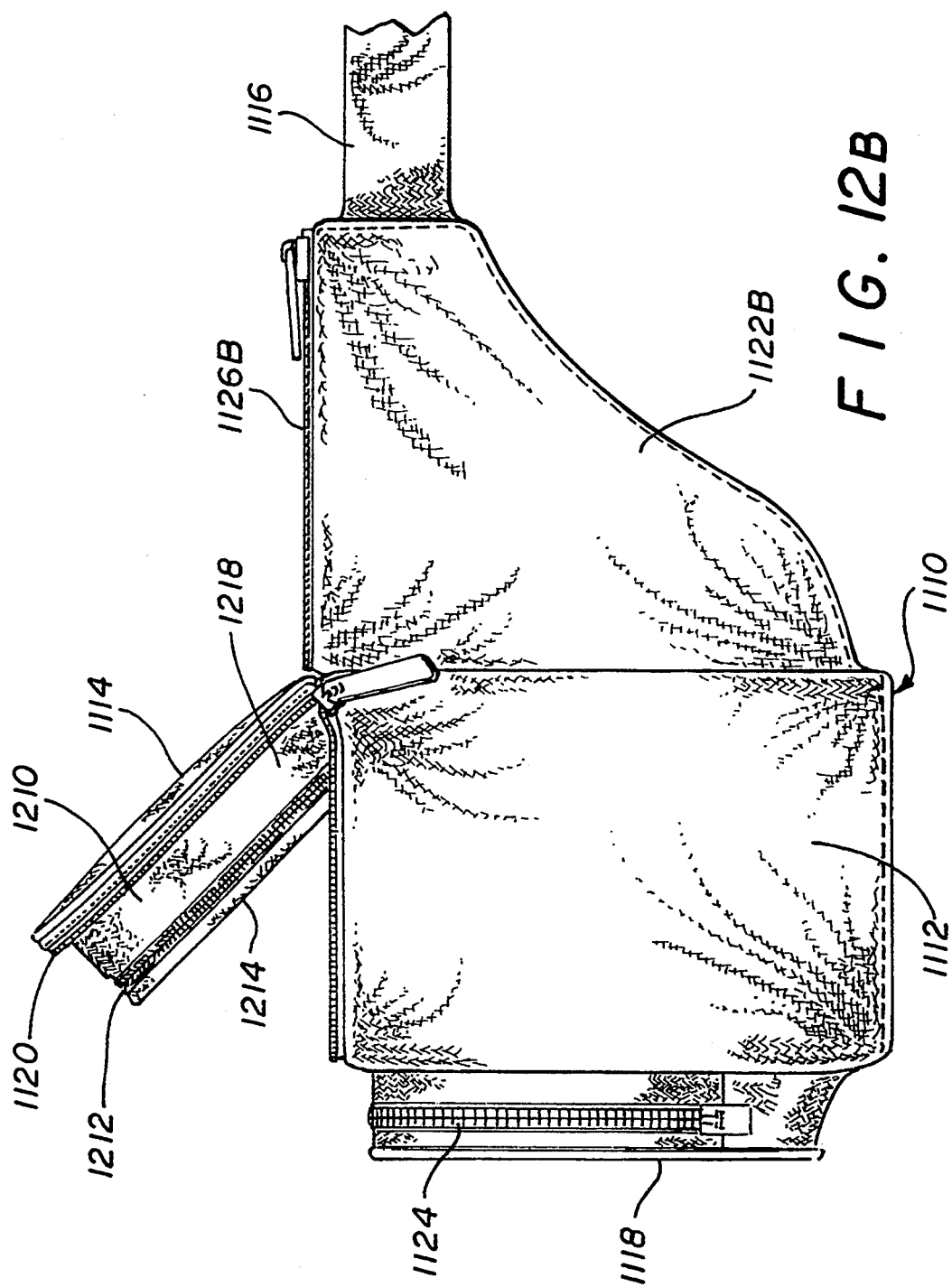

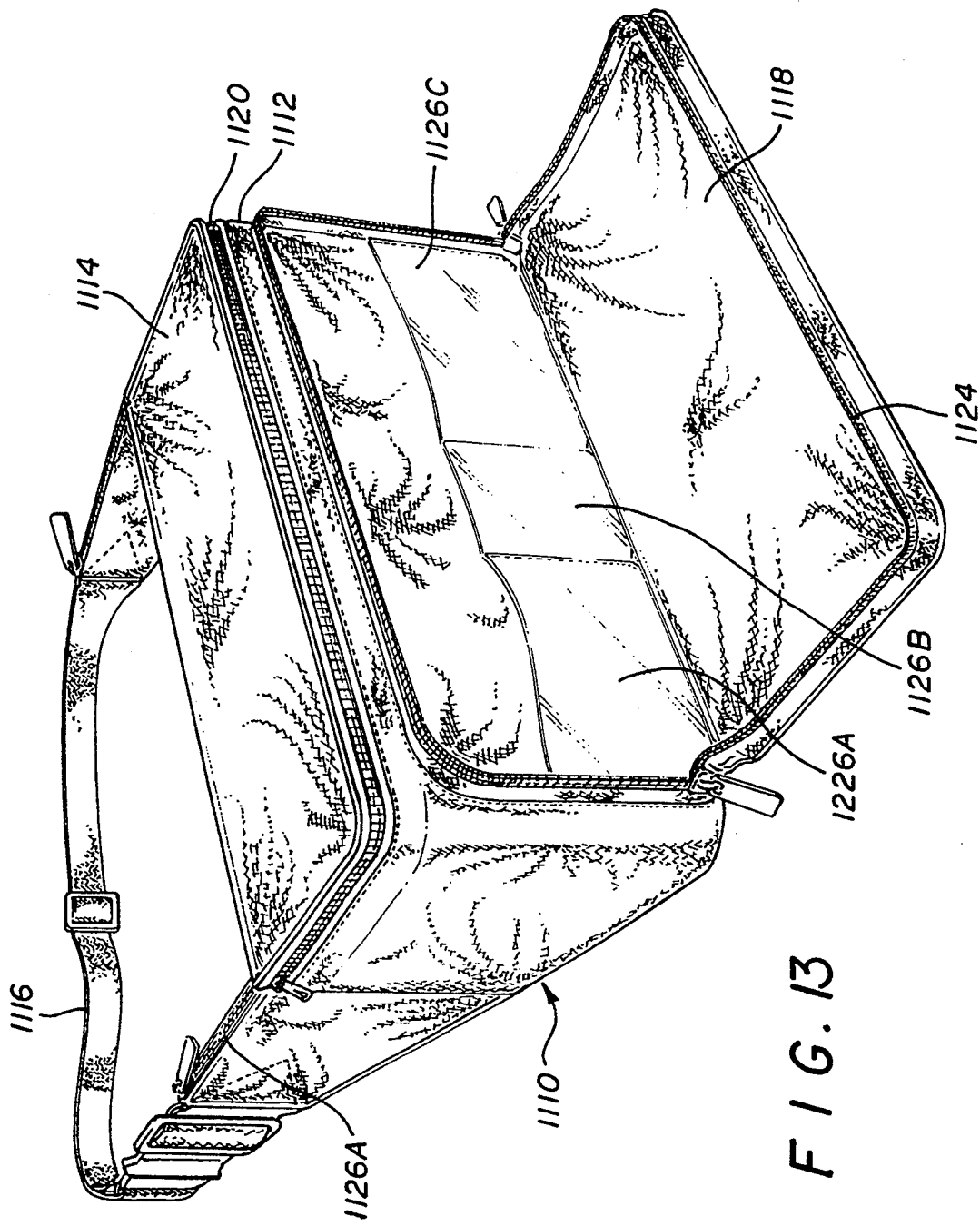

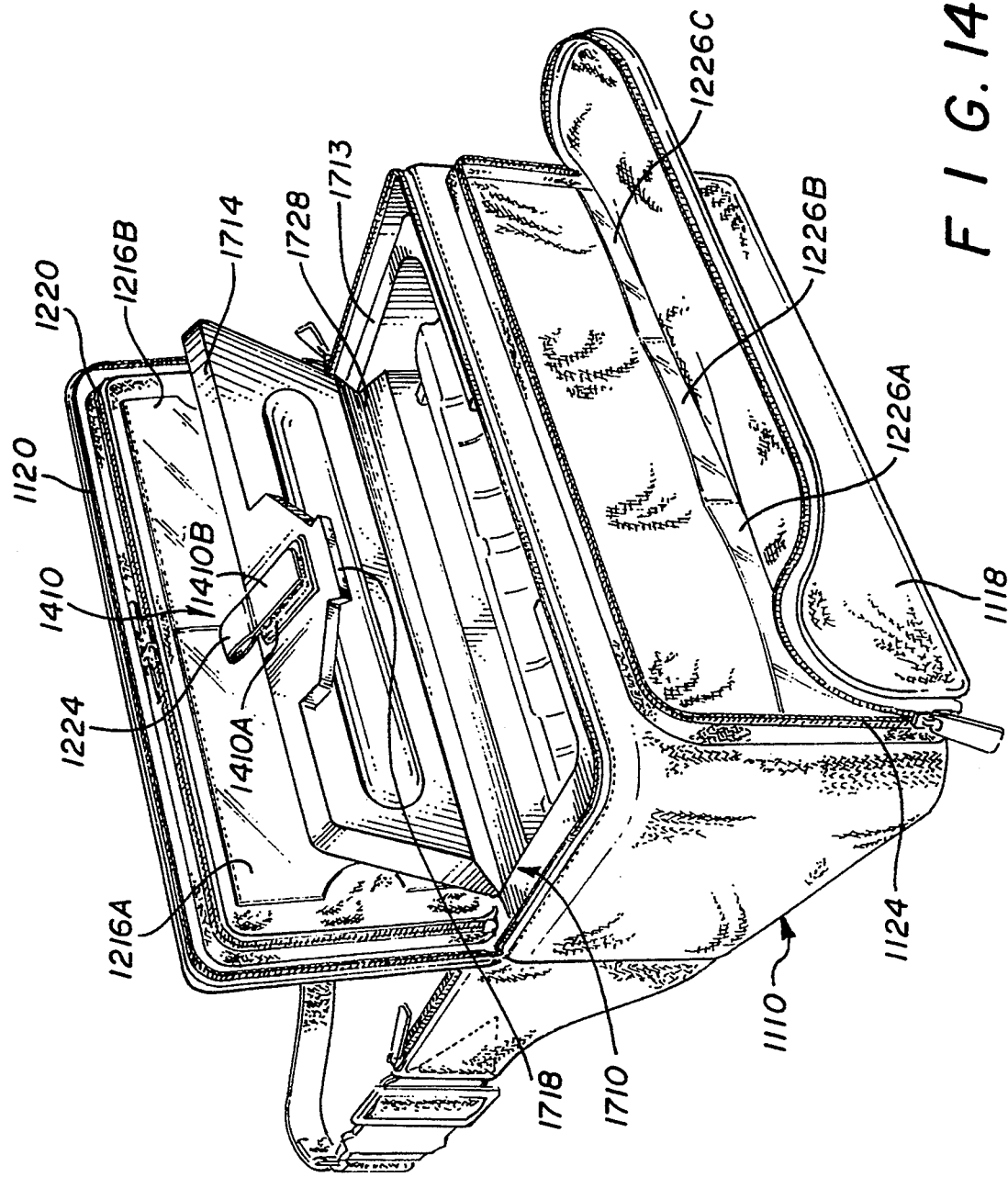

TEMPERATURE CONTROLLED MEDECINE CARRIER

BACKGROUND OF THE PRESENT INVENTION

1. Field of the Invention

The present invention relates to the field of portable containers for transporting medicine vials of differing sizes and protecting them from environmental damage. In particular, the present invention is directed to a container for transporting liquid medicine in a temperature controlled environment.

2. Background Art

There are certain physical conditions or ailments, such as diabetes, allergies, etc. that require regular applications of medicine. In addition, it may also be required that certain counteractive agents be available should emergency situations arise. For example, a person who is allergic to wasp stings must have quick access to medication in case of a wasp sting. In addition, regular and repeated applications of medication may be required, either orally or through injection. Persons with diabetes take insulin by injection, in order to control blood sugar level. Other physical conditions may also require the repeated application or availability of medication either on a life long or temporary basis.

Many medications, however, are subject to rapid degradation of their beneficial properties as a result of temperature and other environmental conditions. Other medications may be sensitive to light and still others may be sensitive to a combination of light and temperature. Further, many types of medication, particularly those taken by injection are stored in glass vials or bottles which are subject to breakage if dropped or otherwise traumatized.

As a result, the mobility of those people requiring a constant availability of medication is severely restricted. For example, for one allergic to insect bites, medication must be administered within minutes and sometimes seconds after an insect bite to prevent severe complications or even death. Likewise, a diabetic must remain near a source of insulin in order to receive regular injections or an emergency injection should blood sugar level dictate. Therefore, it is desired to provide a means of storing medication such as wasp sting serum and insulin along with means of administering it in a protective carrying case so that people who require medication may travel about with a supply of such medication.

However, insulin for example, like many other medications must be kept cold in order to maintain its effectiveness. Therefore, people who wish to travel about in warm temperature require some means of transporting insulin in a temperature controlled environment to maintain it at a desired temperature.

In addition, insulin manufacturers warn against freezing insulin. Therefore, it is desired to provide a means of transporting insulin in cold weather which will prevent it from reaching the Freezing point. Thus, a portable medicine protector is desired to keep cool temperature in and keep freezing temperatures out.

Another difficulty is that medicine is typically kept in glass vials which come in a variety of different shapes and sizes. By way of example, a person might have need for more than one different type of allergy medicine if they suffer many different allergic reactions. At the same time, although a person may only need a single medication such as insulin, different batches of the medicine may come in different size vials. Finally, it may also be necessary to store the medicine applicator (e.g., a syringe) in the same type of protected container as the medicine itself. Having a different transportation device for each different type of medicine or different size vials is for obvious reasons undesirable. Therefore, any device for transporting the medicine should be able to accommodate different sized and shaped vials and prefilled type syringe-pen systems.

There have been a number of efforts in the prior art to provide a portable medicine carrier and protector for insulin and other medicines. For example, Taylor, U.S. Pat. No. 4,250,998 is directed to a diabetic travel kit comprising an outer insulated container and an inner container having a ring shaped chamber containing coolant. A compartment is provided in the ring shaped chamber for receiving an insulin bottle. The outer container is insulated to help maintain the temperature of the inner chamber.

Campbell, U.S. Pat. No. 4,343,158 discloses a portable pouch for storing insulin and syringes. The pouch includes a central space filled with insulating material and a central space for inserting an ice pack for temperature control. Ehmann, U.S. Pat. No. 4,429,793 is directed to a diabetic traveling case comprising an insulated zippered case. A plastic container filled with liquid is frozen and inserted into the case. Containers of insulin are also inserted into the case next to the frozen container. Sheehan, et al., U.S. Pat. No. 4,322,954 is directed to a portable medicine cooler which has an insulated compartment coupled by means of a heat sink to a second compartment filled with frozen jell, ice or other coolant.

Finally, Yeager, U.S. Pat. No. 4,738,364 discloses a medicine carrier for storing and transporting medicine in a controlled temperature environment. The medicine carrier includes a protective insert which is filled with a liquid such as water or BLUE ICE which is frozen. The protective insert includes a cylindrically recessed area for receiving bottles of insulin. The protective insert is placed within a carrying case.

Although the above patents illustrate the recognized need for a portable medicine carrier and protector, none provides a storage environment which both protects from extremely high as well as extremely low temperatures, while allowing several different medicine vials of differing sizes to be transported.

SUMMARY OF THE PRESENT INVENTION

The present invention provides a portable medicine carrier and protector for storing and transporting medicine stored in vials. The vials may be of different sizes. The medicine carrier and protector includes a hollow, thin walled medicine carrier. The carrier is substantially filled with a paraffinic hydrocarbon (C14–C18) such as Hexadecane, an alpha olefin (C14–C20), or a material such as Dimethyl Sulfoxide. A cavity is disposed in a top surface of the carrier. The cavity defines a plurality of different semicircular compartments. Each of the compartments has a different cross-sectional radius. This allows the carrier to accept medicine vials of differing sizes. A plurality of solid ribbed members are disposed transversely in the cavity, so as to prevent direct contact between the carrier and the medicine vials.

BRIEF DESCRIPTION OF THE DRAWINGS

FIGS. 10A–10B are side and front diagrams illustrating an optional protective outer casing for the carrier;

FIG. 11 is a perspective diagram illustrating the outer case of the present invention;

FIGS. 12A–12C are diagrams illustrating the outer case of the present invention;

FIG. 13 is a diagram illustrating a pocket of the outer case of the present invention;

FIG. 14 is a diagram illustrating the inner case of the present invention enclosed within the outer case;

DETAILED DESCRIPTION OF THE PREFERRED EMBODIMENT

A novel portable medicine carrier and protector is described. In the following description, for the purposes of explanation, specific construction details, arrangements, and component shapes are set forth in order to provide a more thorough understanding of the present invention. It will be apparent to those skilled in the art, however, that the present invention may be practiced without these specific details. In other instances, well known structures, materials and manufacturing methods have not been described in detail so as not to obscure the present invention unnecessarily.

Figure 1:
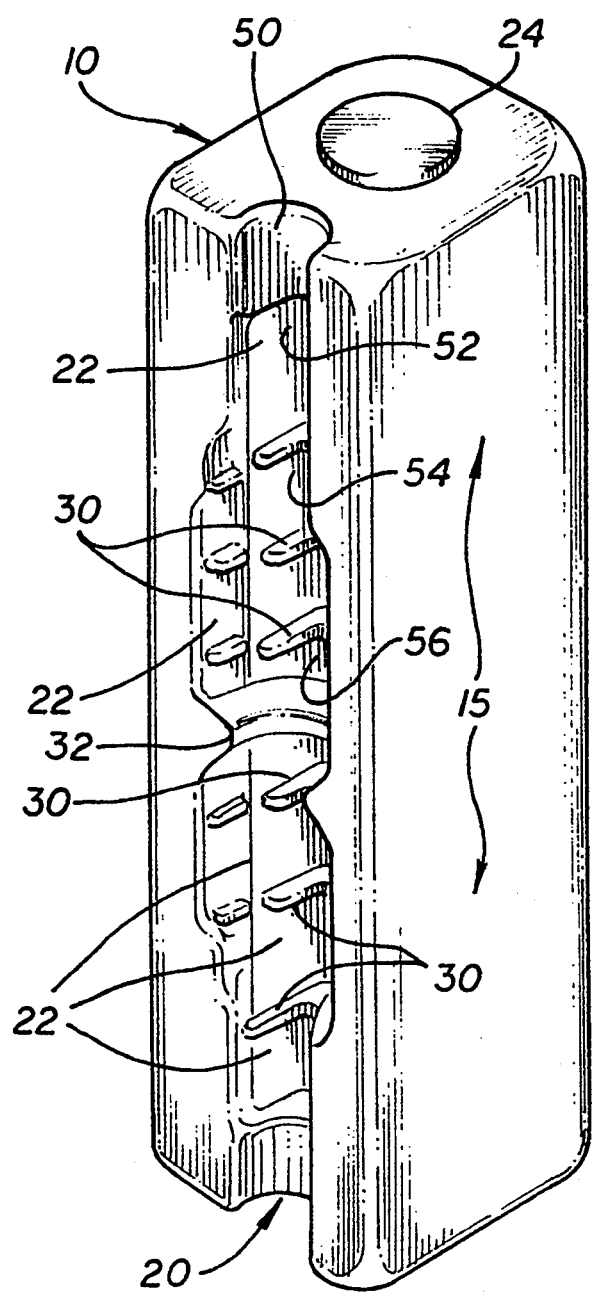
FIG. 1 is a perspective view of the preferred embodiment of the portable medicine carrier of the present invention.

Referring first to FIG. 1, a perspective view of the preferred embodiment of the present invention is illustrated. In the preferred embodiment of the present invention, the medicine carrier 10 is a generally rectangular, thin-walled, hollow structure. The carrier 10 is of such a size that it can be easily carried by a user in a purse or other suitable enclosure. In the preferred embodiment of the present invention, the carrier 10 is made from polyethylene. It will be apparent to those skilled in the art, however, that any material which can be made watertight and has a slight flexibility can be used with equal effectiveness.

The carrier 10 is filled with a liquid 15 that undergoes a phase change (i.e., freezes) at a temperature that is approximately equal to the desired storage temperature of the medicine. In practice, it has been found that a paraffinic hydrocarbon (C14–C18) such as Hexadecane, an alpha olefin (C14–C18), or the material Dimethyl Sulfoxide (DMSO) can be used to fill the storage carrier 10. Hexadecane is an organic based material that freezes at a temperature of approximately 64.8° Fahrenheit. Dimethyl Sulfoxide is an organic based material that freezes at a temperature of approximately 68° Fahrenheit. Although Hexadecane is used in the preferred embodiment, it will be apparent to those skilled in the art that other liquids could be substituted in its place. Substitute liquids would be used when it is desired to store medicine at a temperature different from that achieved by the use of Hexadecane. A stopper 24 seals an opening 26 (not shown) in carrier 10 which is used to allow the Hexadecane to be introduced into the carrier 10.

Referring again to FIG. 1, formed in the top surface of the carrier is a cavity 20. The cavity accepts the vials of insulin and other medicines that the user desires to store and transport in a temperature controlled environment. The cavity 20 is not of a uniform cross-section, but is made up of a number of distinct compartments 22. These compartments 22 are of different sizes so as to accommodate a wide variety of medicine vials, thereby maximizing the effectiveness and usage of the present invention.

Figure 2:
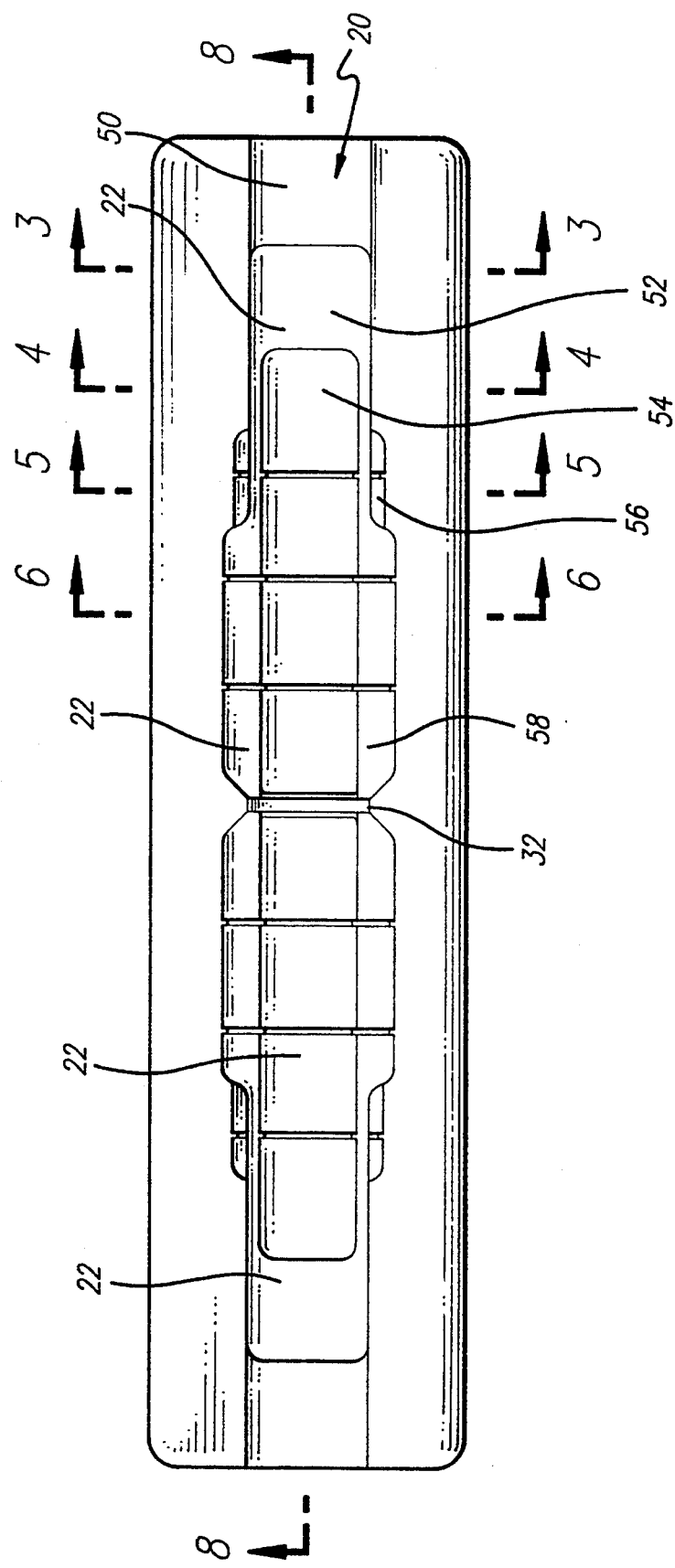
FIG. 2 is a plan view of the top of the portable medicine carrier.

In FIG. 2, a plan view of the top of the carrier 10 is shown. As can be seen, the cavity 20 runs longitudinally down the length of the carrier 10. The width of the cavity 20 is not constant, but varies according to the size of the different compartments 22.

In FIG. 2, several cross-sectional views are represented by lines 3—3, 4—4, 5—5, 6—6, and 8—8. The lines indicate cross-sectional views of carrier 10 shown in FIGS. 3 through 6 and 8. The drawing of carrier 10 illustrated in FIG. 2 provides a top view of cavities 22, wherein the cavities 22 are shown to have several radii indicated in FIGS. 3 through 6.

Referring next to FIGS. 3 through 6 a number of different cross-sectional views of the carrier 10 are shown. The cross sections are taken at the locations indicated by the dashed lines in FIG. 2. As can be seen, the cavity 20 is generally semi-circular in cross section. However, the compartments 22 each have different dimensions so as to accommodate the different size vials. It has been found that in order to provide the optimum usefulness of the present invention, the circular cross sections of the compartments 22 should have dimensions approximately equal to those indicated in FIGS. 3 through 6. These particular dimensions allow the present invention to be used with the most common sizes of medicine vials and applicators in use at the present time.

Figure 3:
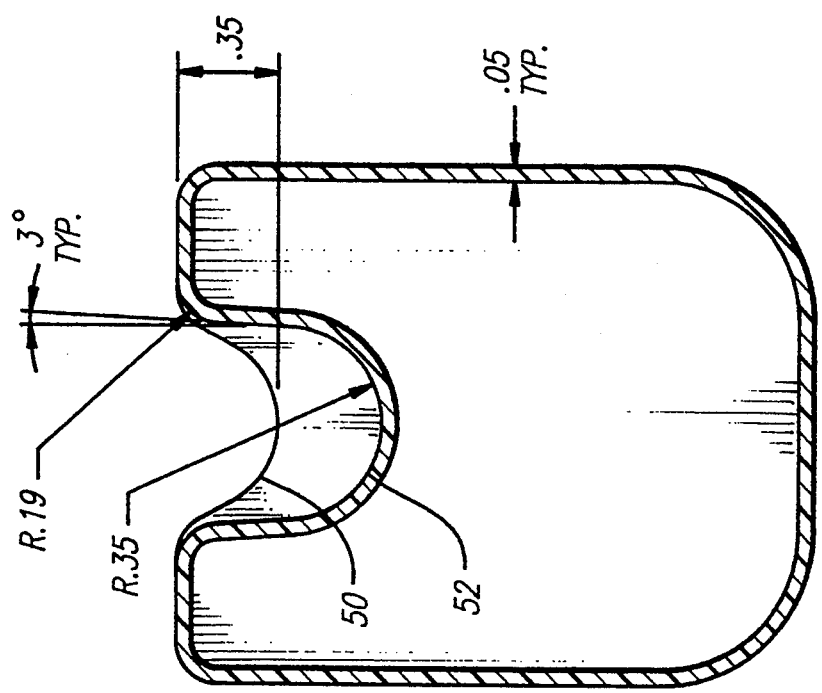
FIG. 3 is a cross sectional view of the carrier taken along the line 3—3 in FIG. 2, showing the dimensions of one of the compartments in the preferred embodiment.

FIG. 3 is a cross-sectional view of lip 50 and compartment 52 which are included within compartments 22. Outer lip 50 is shown to be at a typical depth of 0.35 inches relative to the top surface of carrier 10 (illustrated by two arrows and a pair of lines). Compartment 52 is shown to have a radius of 0.35 inches centered at a depth of 0.35 inches relative to the top surface of carrier 10. The diagram also illustrates a typical wall thickness of 0.05 inches.

Figure 4:
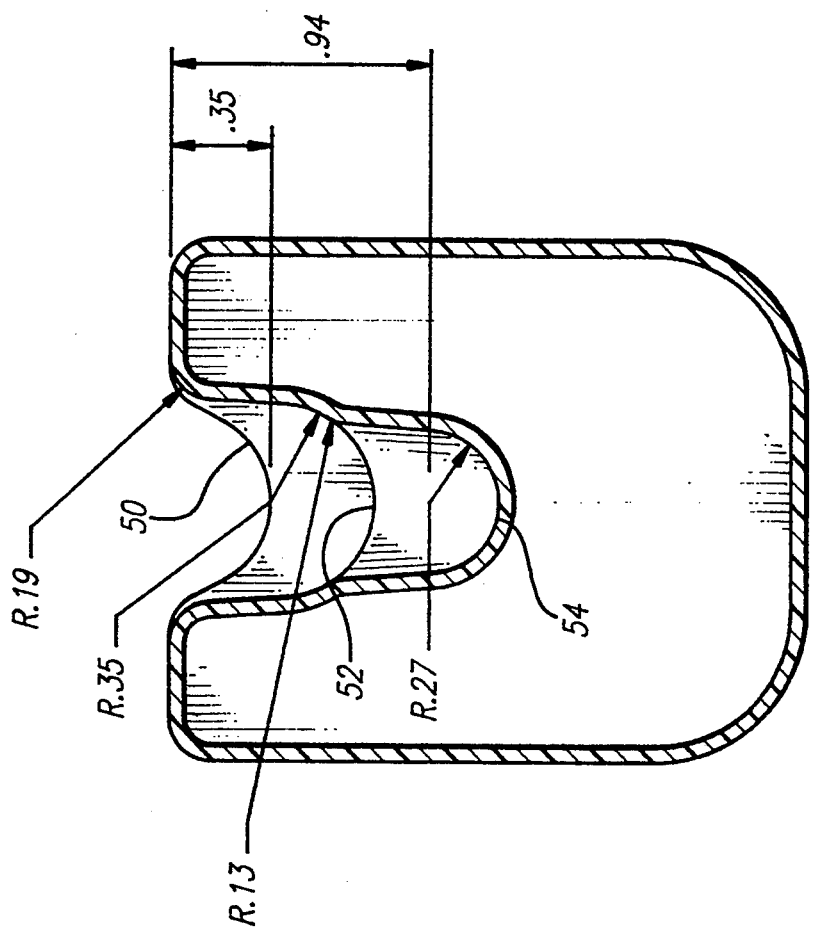
FIG. 4 is a cross sectional view of the carrier taken along the line 4—4 in FIG. 2, showing the dimensions of one of the compartments in the preferred embodiment.
Figure 6:
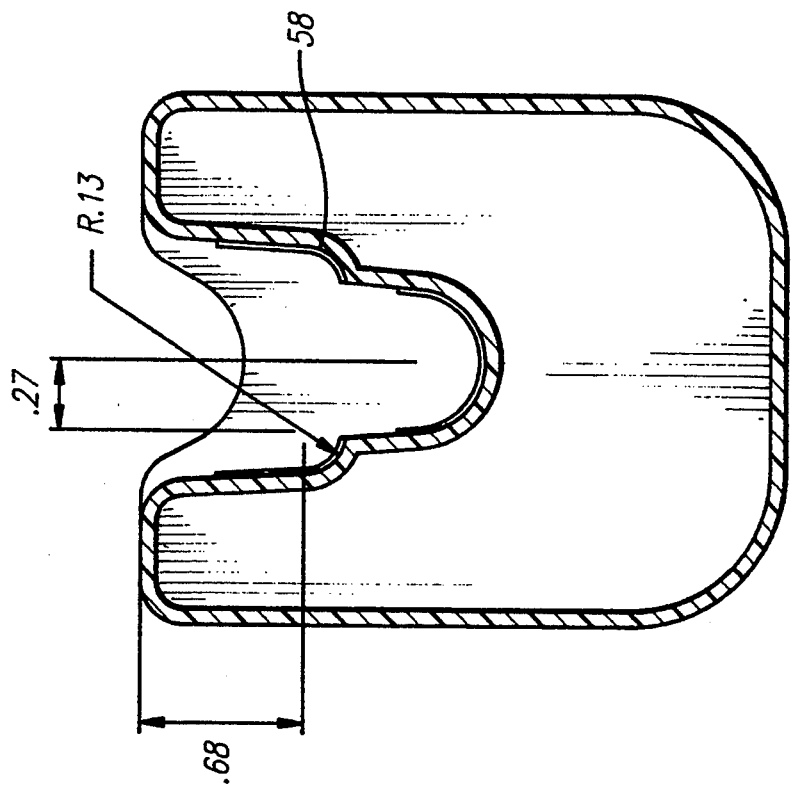
FIG. 6 is a cross sectional view of the carrier taken along the line 6—6 in FIG. 2, showing the dimensions of one of the compartments in the preferred embodiment.
Figure 5:
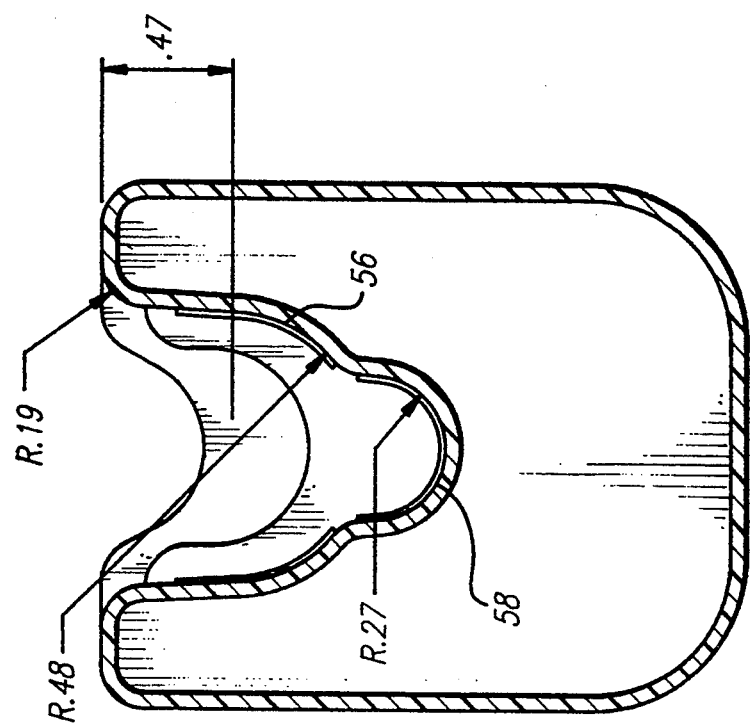
FIG. 5 is a cross sectional view of the carrier taken along the line 5—5 in FIG. 2, showing the dimensions of one of the compartments in the preferred embodiment.

FIG. 4 is a cross-sectional view of compartments 52-54 which are included within compartments 22. Compartment 52 is as shown in FIG. 3. Compartment 54 is shown to have a radius of 0.27 inches at a depth of 0.94 inches. FIG. 5 is a cross sectional view of compartment 56. Compartment 56 is centered at a depth of 0.47 inches and has a radius of 0.48 inches. FIG. 6 is a cross-sectional view of compartment 58 which is included within compartments 22. Ridge 58 is located at a depth of 0.68 inches and has a radius of 0.13 inches.

Although FIGS. 3 through 6 specify certain dimensions for the size of the compartments 22 in the cavity 20, it is to be understood that those dimensions are specified only as an example of the preferred embodiment of the present invention. It will be apparent to those skilled in the art that the exact dimensions of the compartments 22 can be modified or changed without departing from the overall spirit and scope of the present invention. For example, it may be desired to vary the sizes of the compartments 22 in order to allow medicine vials having non-standard or odd sizes to be used with the present invention.

Figure 7:
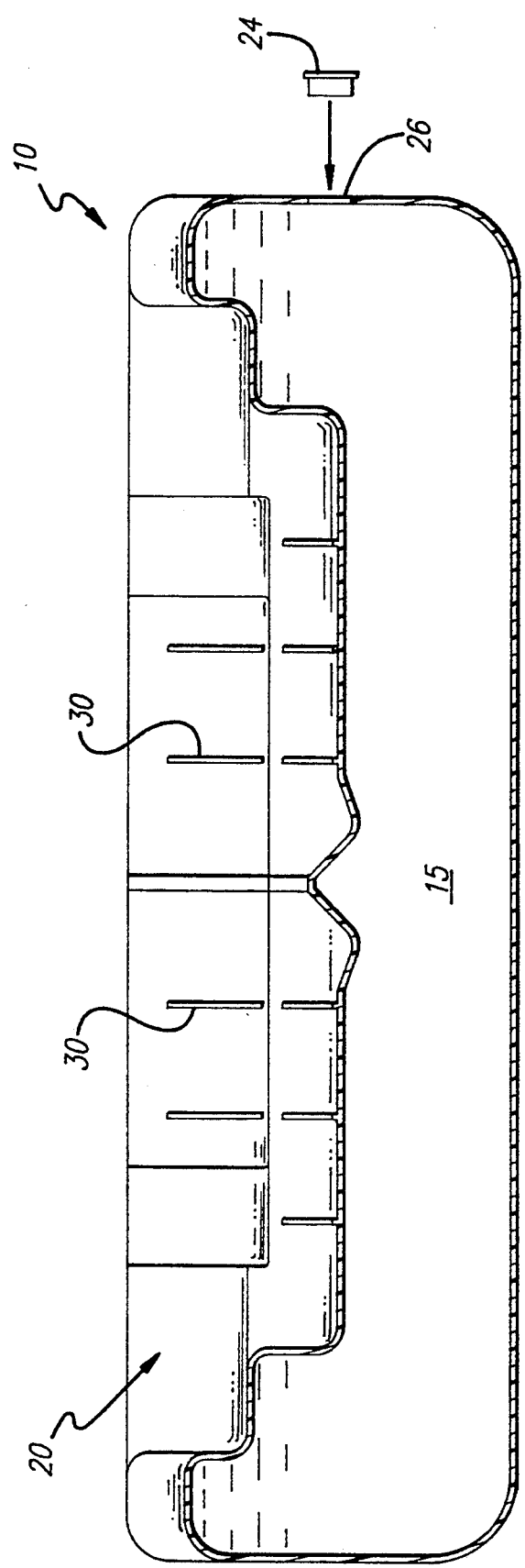
FIG. 7 is a side view of the portable medicine carrier.

Referring next to FIG. 7, a side view of the carrier 10 of the present invention is illustrated. In the preferred embodiment, the carrier is substantially rectangularly shaped in cross section. However, any suitable cross sectional shape may be utilized without departing from the overall spirit and scope of the present invention. A stopper 24 seals an opening 26 in carrier 10 which is used to allow the liquid 15 to be introduced into the carrier. Stopper 24 is disposed approximately in the center of one end of the carrier in the preferred embodiment of the present invention. However, the stopper 24 and corresponding opening 26 may be placed wherever desired.

In the preferred embodiment of the invention, the stopper 24 is fixed permanently in place, but it may be made removable. For example, it may be desired to store different types of medicines at different times. In that case, a removable stopper could allow the carrier 10 to be emptied and a different liquid 15 with different freezing temperature to be introduced in its place.

Figure 8:
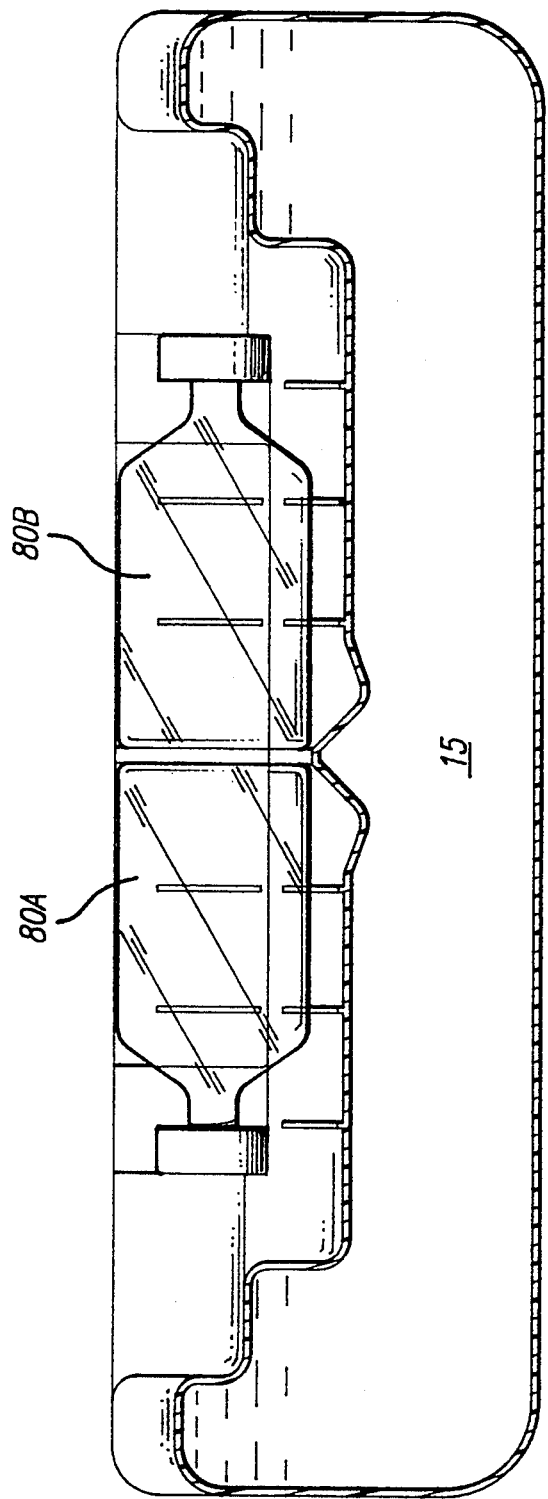
FIG. 8 is a cross sectional view of the carrier taken along the line 8—8 in FIG. 2, showing the carrier holding two standard size bottles of insulin.
Figure 9A:
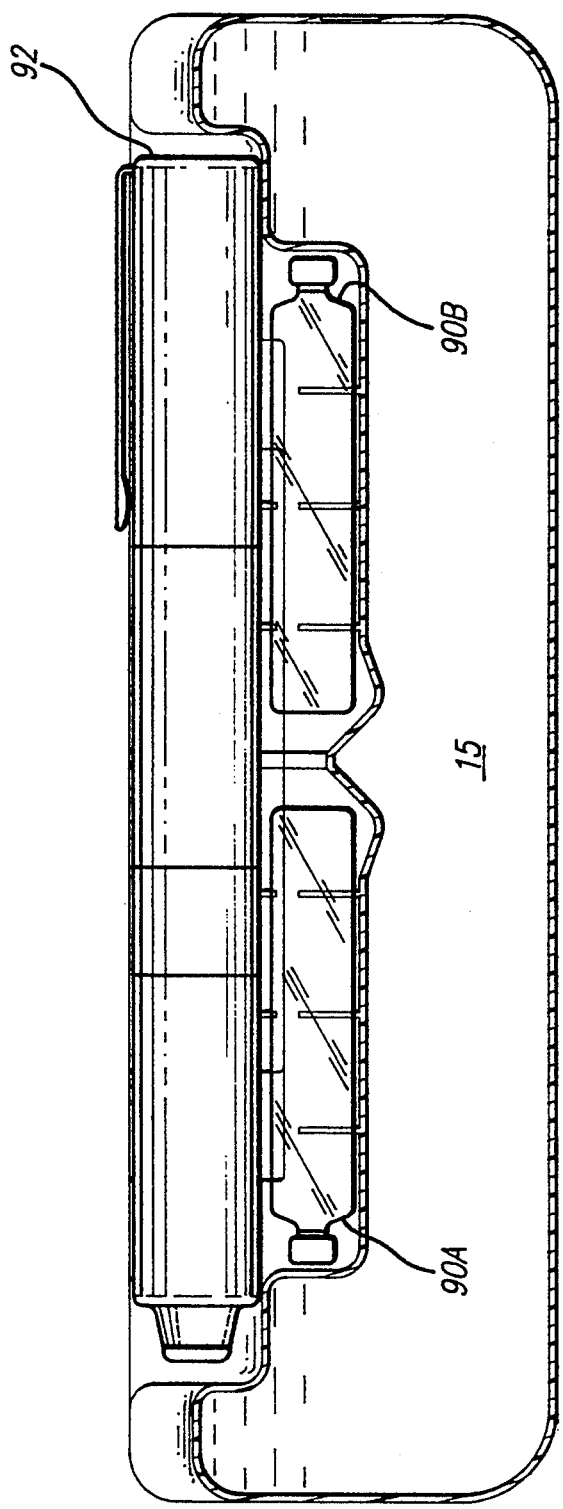
FIGS. 9A–9B are cross sectional views of the carrier 10 taken along the line 8—8 in FIG. 2, showing the carrier holding two bottles 90A–90B of insulin and a medicine applicator 92 and illustrating an inclined medicine vial 90B, respectively.
Figure 9B:
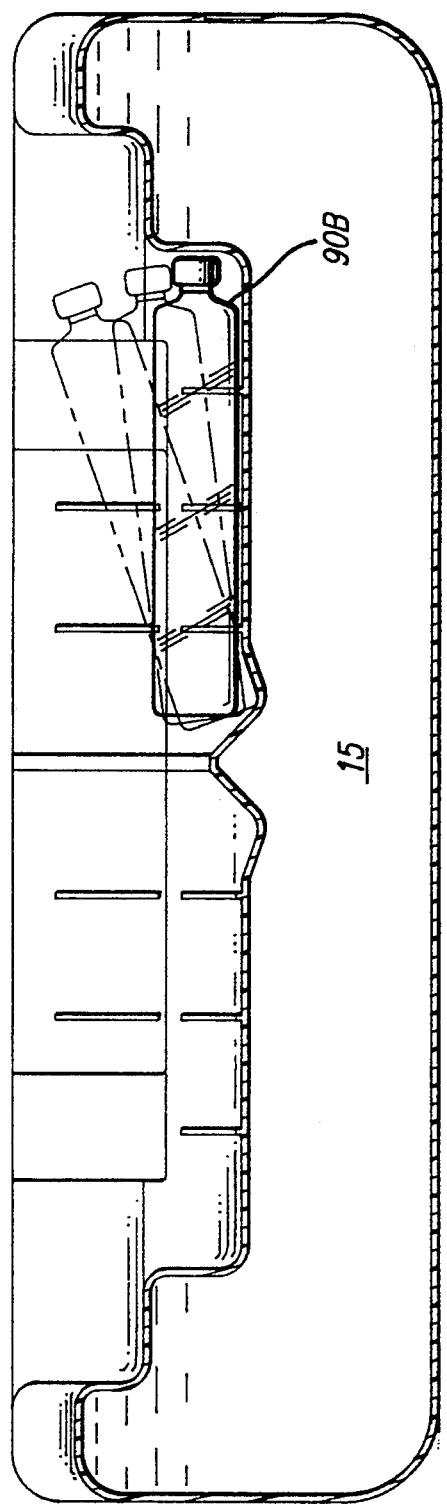

Referring next to FIGS. 8 and 9A-9B, several different cross-sectional views of the carrier 10 holding different sized medicine vials and applicators are shown. Although specific vials and applicators are shown in FIGS. 8 and 9, it is to be understood that these items are presented for illustration only, and do not form a part of the present invention. The invention consists only of the portable medicine carrier and protector, as described herein, and claimed in the following claims. In FIG. 8, the carrier is holding two medicine vials 80A and 80B having a size that are of a standard for insulin. In FIG. 9A the carrier is shown with two smaller vials of medicine 90A-90B, along with an applicator 92 commonly known as the NOVO PEN II insulin pen system. In FIG. 9B, vial 90B is inclined at several angles using carrier 10 that provide ease in accessing the vial 90B.

In operation, the storage carrier is placed in a household refrigerator or freezer for a sufficient time to allow the liquid 15 to freeze. The medicine vials are then placed within the appropriate cavities 22 of the carrier 10. This provides for a temperature controlled environment for storage of the medicine. So long as the liquid 15 remains in a frozen state, its temperature will remain constant, and the temperature of the medicine in the vials will remain near that same value.

It has been found that direct contact between a medicine storage vial and the walls of the carrier 10 may result in the generation of localized "cold spots" in the medicine vial which can lead to freezing and crystallization of the medicine. Most insulin manufacturers recommend against the freezing of insulin. Therefore, the present invention includes a feature that is intended to avoid the chance of inadvertently freezing medicine that is stored in the carrier of the present invention.

Referring again to FIG. 1, a plurality of ribbed members 30 are formed along the side walls of the cavity 20 transverse to the width of the carrier 10. The ribbed members 30 prevent a medicine vial from contacting the side walls of the cavity 20. The ribbed members 30 are made from a solid strip of the material used to form the carrier 10.

It may not be necessary in all cases to provide ribs 30 to prevent direct contact between a medicine vial and the storage carrier 10. For example, if it is desired to store solid medicines in the carrier of the present invention no ribs are necessary. Further, if freezing is not a problem for certain liquid medicines, or if the freezing point of the liquid medicine is sufficiently below the recommended storage temperature of such medicine, no ribs are required. Therefore, the present invention is directed to both carriers having ribs and those without ribs. Moreover, the ribs may have an arrangement different from that illustrated.

Referring again to FIG. 2, the compartments 22 in the cavity 20 are separated by a divider 32. The divider 32 prevents adjacent medicine vials from contacting each other. This reduces the risk of breakage, and provides for temperature control of the medicine. The divider 32, like the ribs 30, runs transverse to the width of the carrier 10. The divider 32 is substantially wider than the ribs.

Referring next to FIGS. 10A-10B, an optional protective outer casing 40 for the carrier 10 is illustrated in side and front views, respectively. The outer casing 40 can be manufactured from any suitable material such as foam or other resilient material. The casing 40 has an inner cavity 150 that is shaped and sized to accommodate the carrier 10; inner cavity 150 is indicated by dotted lines in the drawings. The casing 40 includes a hingedly attached top flap 42. The flap 42 includes a finger divot 44 which allows for easy opening. The flap 42 is held in place by locking tab 46. A pocket (not shown) may be formed on the outside of the casing, for storing syringes, test strips, alcohol and the like. If desired, the flap and pocket may employ VELCRO strips for providing positive closure of the pocket.

Referring to FIGS. 11-14, the drawings illustrate a carrying device according to the preferred embodiment of the present invention. The carrying device is of a form referred to as a "fanny" pack or "belly" pack among other terms. The carrying device of the present invention stores items in a refrigerated environment in contrast to a frozen environment. Further, the carrying device of the present invention comprising carrier 10, outer case 1110, and inner case 1710 provides a rigid frame for securing items. The rigid frame provides protection for enclosed items including injectable medicines including diabetic medicines such as insulin and Acquired ImmunoDeficiency Syndrome (AIDS) medicines such as Interferon. The foregoing medicines are provided by way of example. The present invention provides a secure, refrigerated environment for temperature sensitive medicines and materials. The present invention also advantageously stores film and other temperature sensitive materials.

FIG. 11 is a perspective view illustrating the front of outer case 1110 of the present invention. An outer case 1110 is comprised of a body section 1112, lid section 1114, pocket 1118, and restraining means 1116. A first zipper 1120 in the preferred embodiment fastens body and lid sections 1112 and 1114. While first zipper 1120 is disclosed in the preferred embodiment of the present invention, it should be apparent to a person skilled in the art that any suitable means of joining the body and lid sections may be employed. The body and lid sections 1112 and 1114 comprise a durable material such as nylon fabric.

In the preferred embodiment of the present invention, the body and lid sections 1112 and 1114 form an essentially rectangular apparatus having dimensions of approximately $9\frac{1}{4}$ inches $\times 4\frac{1}{2}$ inches $\times 3\frac{1}{2}$ inches. In the preferred embodiment of the present invention, the restraining means 1116 is an adjustable, belt strap comprised of a similar nylon fabric, and has a circumferential length of up to 56 inches. The present invention is not limited to a particular restraining means or to a circumferential length of 56 inches, and other restraining means or lengths may be utilized without departing from the scope of the present invention. The restraining means 1116 allows the present invention to advantageously carried around the waist or over the shoulder of a user, for example.

A first pocket 1118 may be formed on the outside of case 1110 for storing syringes, glucose meters, test strips, alcohol, and the like. In the preferred embodiment of the present invention, the first pocket 1118 is formed on the front face of case 1110. A second zipper 1124 fastens first pocket 1118 to case 1110. In the preferred embodiment of the present invention, first pocket 1118 comprises the same or similar material as comprises body and lid sections 1112 and 1114. The case 1110 may comprise second and third pockets 1122A and 1122B for storing glucose products, keys, coins, and the like. The second and third pockets 1122A and 1122B couple restraining means 1116 and case 1110. Second and third pockets 1122A and 1122B have third and fourth zippers 1126A and 1126B for fastening the pockets 1122A and 1122B, respectively.

FIG. 12A is another perspective view diagram illustrating the present invention. In the drawing, first zipper 1120 is unfastened, and case 1110 is opened. This diagram illustrates that lid section 1114 includes a fourth pocket 1210. Fourth pocket 1210 includes upper section 1218 and bottom section 1214. Fourth pocket 1210 is a hidden pocket in lid section 1114. Fifth zipper 1212 fastens upper section 1218 and bottom section 1214. The bottom section 1214 further includes a first and second slotted holders 1216A and 1216B for storing identification cards, credit cards, pictures, documents, and the like. First and second holders 1216A and 1216B comprise a clear, durable material such as plastic or vinyl. Alternatively, the first and second holders 1216A and 1216B of the present invention may be implemented using opaque or semi-opaque, durable material.

Lower section 1112 of case 1110 forms a cavity. A second lid section 1220 is disposed substantially within the lower section 1112 at a depth essentially equal to the thickness of fifth pocket 1210. Thus, when the case 1110 is closed, fourth pocket 1210 fits substantially within a first void above second lid section 1220 formed by the sides of lower section 1112 and second lid section 1220. The second lid section 1220 further includes a third holder 1224 for storing identification cards, credit cards, pictures, documents, and the like. Third holder 1224 comprises a clear, durable material such as plastic or vinyl. Alternatively, the third holder 1224 of the present invention may be implemented using opaque or semi-opaque, durable material. Lifting means 1222 is integrally attached to second lid section 1220. Lifting means 1222 is a loop of durable nylon material in the preferred embodiment of the present invention.

In FIG. 12A, the second zipper 1124 is unfastened, and first pocket 1118 is opened. The front of case 1110 includes a third, fourth, and fifth slotted holders 1226A, 1226B, and 1226C for storing identification cards, credit cards, documents, film and the like. Third, fourth, and fifth slotted holders 1226A, 1226B, and 1226C comprise a clear, durable material such as plastic or vinyl. Alternatively, the third, fourth, and fifth slotted holders 1226A, 1226B, and 1226C of the present invention may be implemented using opaque or semi-opaque, durable material.

FIG. 12B is side-view illustrating the right-side of case 1110. First zipper 1120 is unfastened, and the case 1110 is oftened. Second zipper 1124 is fastened, and first pocket 1118 is closed. Optional third pocket 1122B is shown coupling fastening means 1116 and lower section 1112 of case 1110. Fourth zipper 1126B is shown on the upper surface of third pocket 1122B. Lid section 1114 is shown angularly disposed illustrating fourth pocket 1210 in side-view. Fifth zipper 1212 is fastened, and fourth pocket 1210 is closed. Thus, upper section 1218 and lower section 1214 of fourth pocket 1210 are coupled together.

Figure 12C:
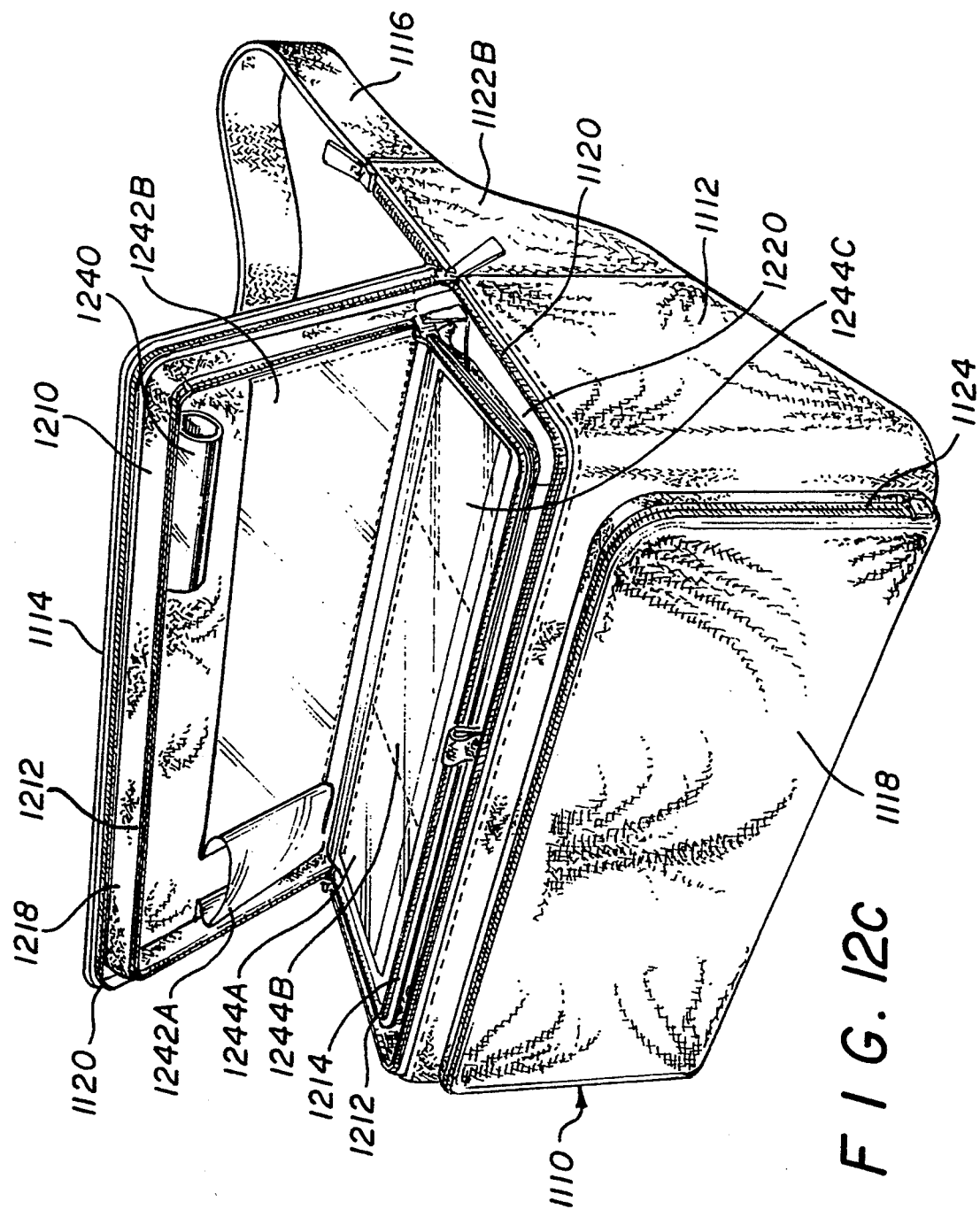

FIG. 12C is a perspective view diagram illustrating fourth pocket 1210. Fifth zipper 1212 is unfastened, and the fourth pocket 1210 is opened. Upper section 1218 of fourth pocket 1210 includes a cylindrical holder 1240 for holding lancing devices, pens, etc. Cylindrical holder 1240 is comprised of durable nylon material in the preferred embodiment of the present invention. Upper section 1218 of fourth pocket 1210 includes a sixth holder 1242B and a holding loop 1242A that is essentially cylindrical for holding test strips, lancing devices, alcohol wipes, cotton balls, syringes, films, and the like. Holding loop 1242A and sixth holder 1242B comprise a clear, durable material such as plastic or vinyl. Alternatively, the holding loop 1242A and sixth holder 1242B of the present invention may be implemented using opaque or semi-opaque, durable material. The inner surface of bottom section 1214 includes a seventh, eighth, and ninth slotted holders 1244A, 1244B, and 1244C for storing identification cards, credit cards, documents, film and the like. Seventh, eighth, and ninth slotted holders 1244A, 1244B, and 1244C comprise a clear, durable material such as plastic or vinyl. Alternatively, the seventh, eighth, and ninth slotted holders 1244A, 1244B, and 1244C of the present invention may be implemented using opaque or semi-opaque, durable material.

FIG. 13 is yet another diagram illustrating first pocket 1118 as in FIG. 12A. Second zipper 1124 is unfastened, and first pocket 1118 is opened. As described above, the front of case 1110 includes third, fourth, and fifth slotted holders 1226A, 1226B, and 1226C for storing identification cards, credit cards, documents, film and the like.

FIG. 14 is a perspective diagram illustrating outer case 1110 and inner case 1710 of the present invention. Inner case 1710 is a rigid body for storing carrier 10 that is substantially contained in a second void of outer case 1710. The second void of outer case 1710 is defined by the side and bottom, inner surfaces of outer case 1110 and the bottom surface of second lid section 1220. In FIG. 14, second lid section 1220 is fastened to lid 1714 of inner case 1710 by lid attachment means 1410. In the preferred embodiment of the present invention, the lid attachment means 1410 for coupling second lid section 1220 of outer case 1110 and lid 1714 of inner case 1710 comprises VELCRO strips 1410A and 1410B. Further, in the preferred embodiment of the present invention, VELCRO strip 1410B is an integral component of lifting means 1224. The present invention is not limited to VELCRO strips for coupling second lid section 1220 and lid 1714, and other attachment means may be utilized without departing from the scope of the present invention.

Figure 15:
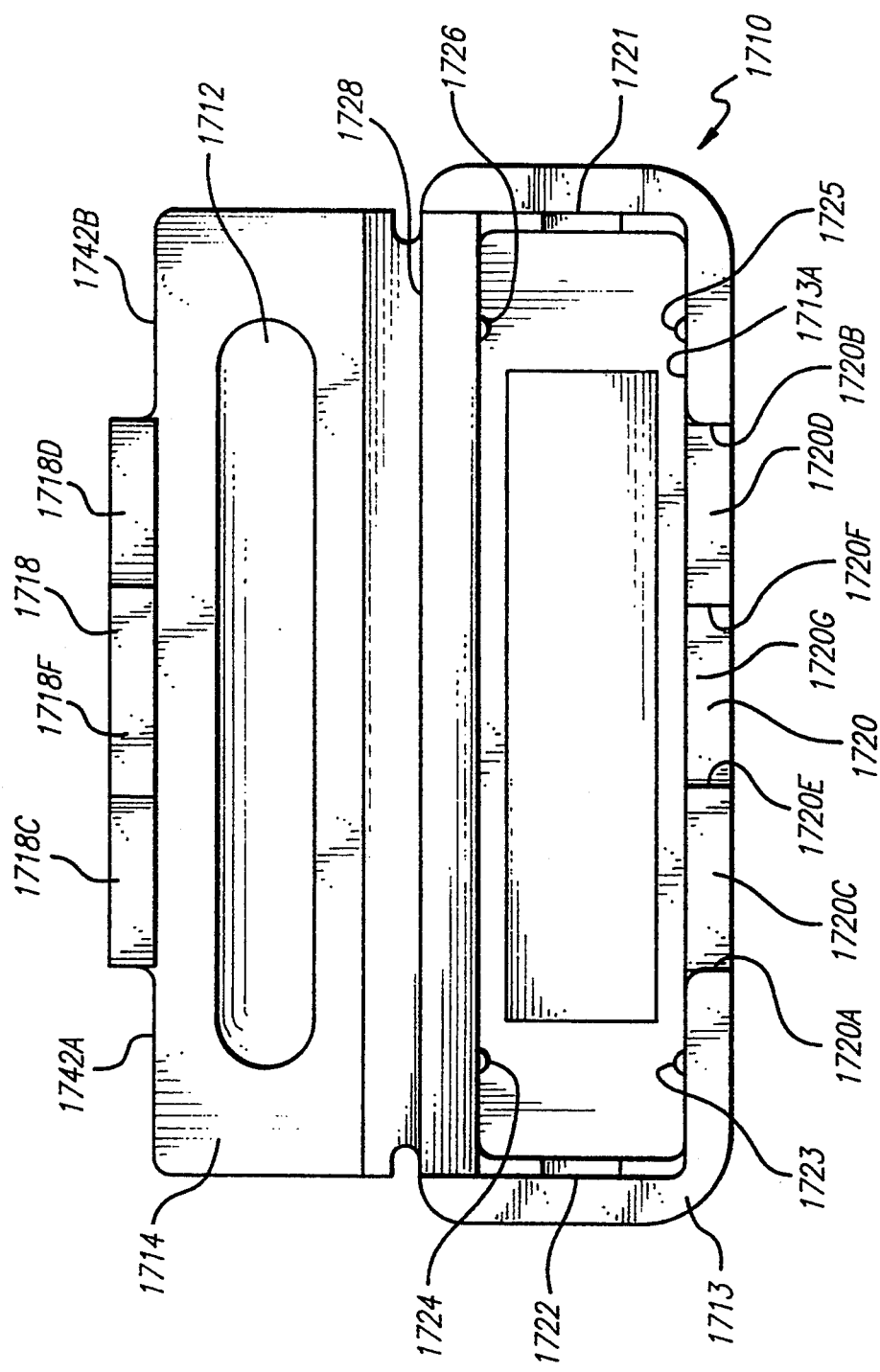
FIG. 15 is a top-view diagram. illustrating the inner case of the present invention.
Figure 16:
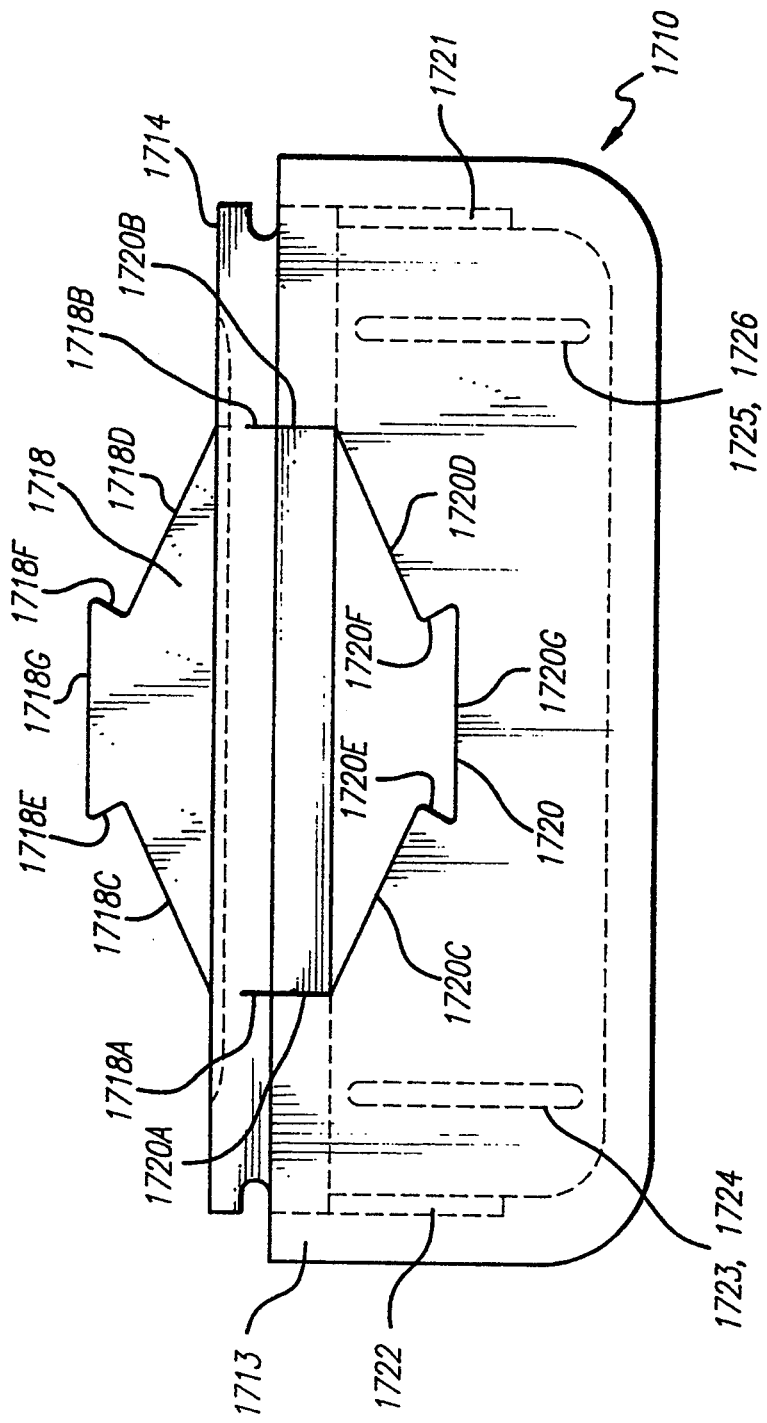
FIG. 16 is a front-view diagram illustrating, the inner case of the present invention.
Figure 17:
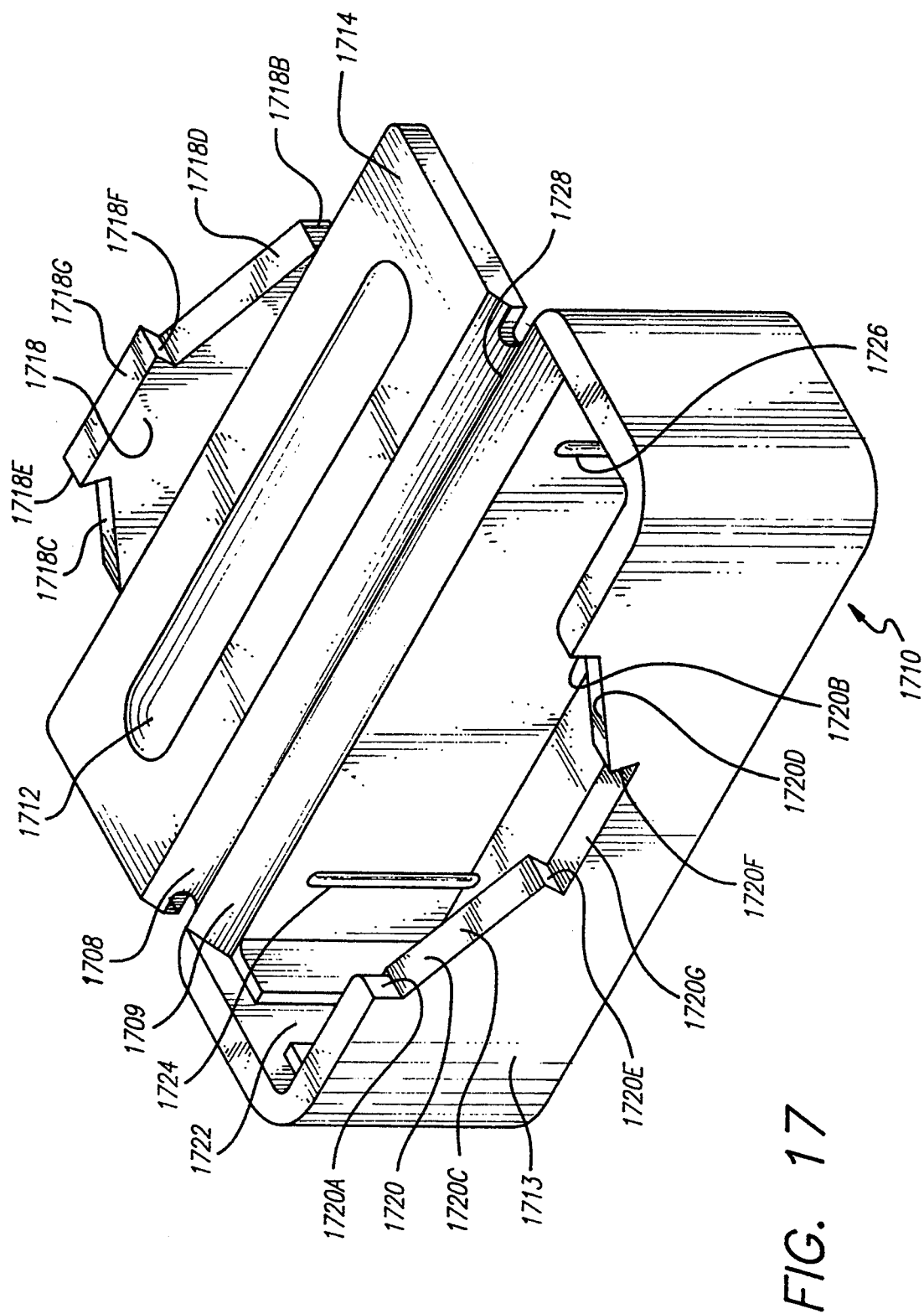
FIG. 17 is a perspective diagram illustrating the inner case of the present invention; and, FIG. 18 is a side-view diagram illustrating the inner case of the present invention.
Figure 18:
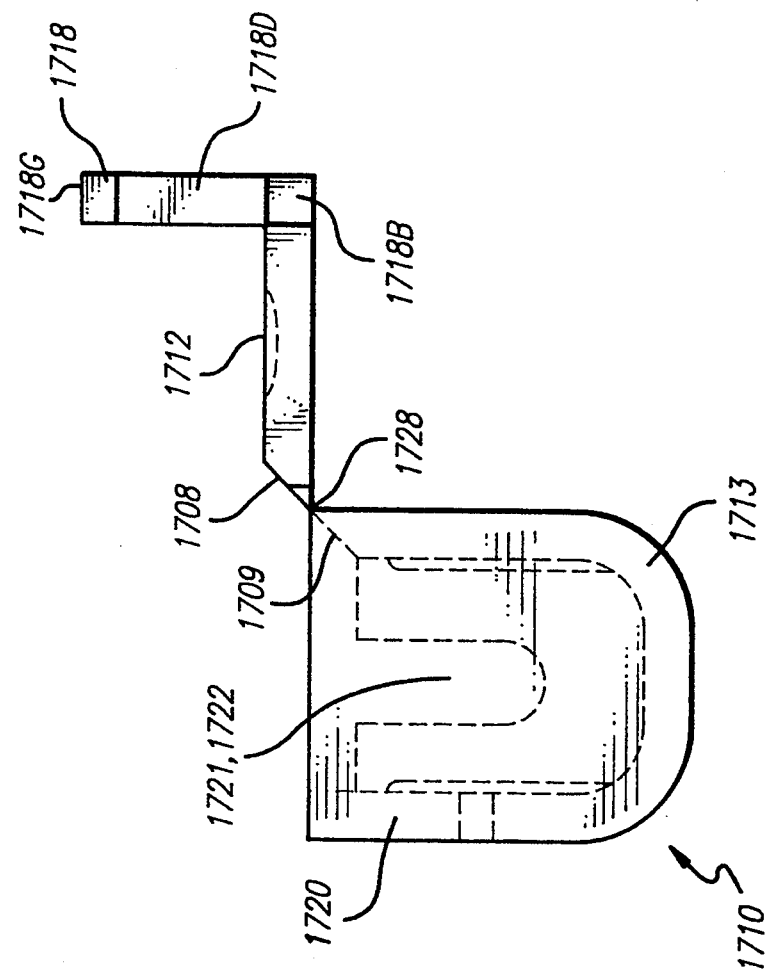

FIGS. 15-18 are diagrams illustrating an inner case 1710 of the present invention. FIG. 17 is a diagram illustrating a perspective view of the inner case 1710. Inner case 1710 comprises a lid section 1714 that is hingedly connected to the body of case 1710 by living hinge 1728. A living hinge is a built-in hinge in inner case 1710 that is located on the upper, outside, rearward portion of case 1710. Inner case 1710 is a monolithic body of insulating foam. The insulating foam acts to prevent, retard, and inhibit the transfer of thermal energy between the inner void of inner case 1710 and the outer surfaces of case 1710. Inner case 1710 is an essentially rigid body for enclosing carrier 10. FIGS. 15, 16, and 18 are top-, front-, and side-views of the inside case 1710 of the present invention.

FIGS. 17 and 18 illustrate the living hinge 1728 of inner case 1710. In FIG. 17, the living hinge 1728 couples lid 1714 to the body 1713 of inner case 1710. As indicated in FIG. 18, surfaces 1708 and 1709 of living hinge 1728 are beveled surfaces with respect to the lid 1714 and rearward portion of body. 1713. Living hinge 1728 allows lid 1714 to be flexibly opened and closed with respect to body 1713 of inner case 1710. When case 1710 is closed, the inner surfaces of case 1710 define an inner void. Beveled surfaces 1708 and 1709 are flush with each other when lid 1714 is closed. Carrier 10 fits substantially within the void defined by body 1713 and lid 1714.

FIGS. 15, 16, and 17 provide top-, front-, and perspective views of locking tab 1718 and notch 1720 for fastening lid 1714 and body 1713 of inner case 1710. As indicated in the diagrams, locking tab 1718 and notch 1720 are reciprocally formed so that locking tab 1718 fits substantially within notch 1720 to fasten lid 1714 and body 1713 of inner case 1710. Locking tab is formed so that surfaces 1742A and 1742B of lid 1714 fit substantially within the inner surface of inner surface 1713A of body 1713 when lid 1714 is closed, as illustrated in FIG. 15. FIG. 15 provides a top-view of inner case 1710 with lid 1714 open. As illustrated in FIGS. 15, 16, anti 17, notch 1720 comprises a plurality of surfaces 1720A-1720G that are reciprocal in form to the surfaces of locking tab 1718 comprising surfaces 1718A-1718G.

Referring to FIG. 16, surfaces 1720A and 1720B of notch 1720 extend downward to a depth equal to the thickness of lid 1714. Surfaces 1718A and 1718B of locking tab 1718 are substantially in contact with surfaces 1720A and 1720B of notch 1720 when lid 1714 is closed. Surface 1720C extends downward toward the right at an acute angle from vertically aligned surface 1720A. Surface 1720D extends downward toward the left at an acute angle from vertically aligned surface 1720B. Surface 1720C of notch 1720 extends to surface 1720E. Surfaces 1720C and 1720E form an obtuse angle. Thus, surface 1720E of notch 1720 extends downward toward the left, thereby forming a securing junction due to the obtuse angle between surfaces 1720C and 1720E. Surface 1720D of notch 1720 extends to surface 1720F. Surfaces 1720D and 1720F form an obtuse angle. Thus, surface 1720F of notch 1720 extends downward toward the right, thereby forming a securing junction due to the obtuse angle between surfaces 1720D and 1720F. Surface 1720F joins surface 1720G of notch 1720.

As described above the surfaces 1718A-1718G of locking tab 1718 are reciprocally formed with respect to surfaces 1720A-1720G, respectively. Thus, lid 1714 and body 1713 are secured together when the surfaces 1718A-1718G of locking tab 1718 are in contact with the respective surfaces 1720A-1720G of notch 1720. The top, outer surface of lid 1714 is flush with the upper, outer surfaces of body 1713 when lid 1714 is closed.

Referring to FIG. 17, the inner surface of lid 1714 defines a recess 1712 that is approximately half cylindrical in shape. The cylindrical recess 1712 formed within the inner surface of lid 1714 runs length-wise in the longest dimension of inner case 1710. Recess 1712 of case 1710 aligns with cavities 22 of carrier 10, with carrier 10 positioned with inner case 1710, to secure a variety of medicine vials that are stored in carrier 10 when lid 1712 is closed. Recess 1712 is further illustrated in lid 1712 in FIG. 18. Inner case 1710 contains ribs 1723-1726 disposed upon the front and back interior surfaces of inner case 1710 that define the aforesaid void. While FIGS. 15-18 illustrate ribs 1723-1726 on the front and back, inner surfaces of inner case 1710, this need not be the case. Any suitable configuration of raised members formed in the inner surfaces of inner case 1710 to secure carrier 10 in the inner case 1710 may be utilized.

In FIGS. 15, 16, and 17, recesses 1721 and 1722 are shown on left and right, inner surfaces of inner case 1710 for receiving stopper 24 of carrier 10. When carrier 10 is contained in inner case 1710, stopper 24 alternately extends into recess 1721 or 1722 dependent upon the orientation of carrier 10.

Accordingly, a novel carrier for storing and transporting medicine in a temperature controlled environment has been described. This description has been made with reference to specific exemplary embodiments thereof. It will, however, be readily apparent to those skilled in the art that various modifications and changes may be made thereto without departing from the overall spirit and scope of the invention. The specification and accompanying drawings, therefore, are to be regarded as illustrative rather than restrictive. The full scope of the present invention is limited only by the following claims.

I claim:

1. A portable medicine protector for storing and transporting medicine stored in vials comprising:
   a hollow, thin walled medicine carrier, said medicine carrier being substantially filled with a liquid medium;
   a cavity disposed in a top surface of said carrier, said cavity being formed from a plurality of different semi-circular compartments;

wherein each of said compartments has a radius chosen to accept medicine vials of a specific size;

a plurality of solid ribbed members disposed transversely in said cavity, so as to prevent contact between said carrier and said medicine vials.

2. The device of claim 1 wherein said carrier is made from polyethylene.

3. The device of claim 1 including an outer case for enclosing said hollow, thin walled medicine carrier.

4. The device of claim 1 wherein said medicine comprises insulin.

5. The device of claim 1 wherein said liquid medium is a paraffinic hydrocarbon.

6. The device of claim 1 wherein said liquid medium is Hexadecane.

7. The device of claim 1 wherein a temperature of said liquid medium is approximately equal to 64° Fahrenheit.

8. The device of claim 1 wherein said liquid medium is a alpha olefin.

9. The device of claim 1 wherein said liquid medium is Dimethyl Sulfoxide.

10. The device of claim 1 wherein a temperature of said liquid medium is approximately equal to 68° Fahrenheit.

* * * * *